United States Patent [19]

Anderson et al.

[11] Patent Number: 5,059,696
[45] Date of Patent: Oct. 22, 1991

[54] PROCESSES AND INTERMEDIATES FOR THE PREPARATION OF 5-OXYGENATED HMG-COA REDUCTASE INHIBITORS

[75] Inventors: Robert K. Anderson, Plainsboro; Ann E. DeCamp, N. Plainfield; Alan T. Kawaguchi, Berkeley Heights; Anthony O. King, Hillsborough; Sander G. Mills, Woodbridge; Ralph P. Volante, East Windsor, all of N.J.

[73] Assignee: Merck & Co., Inc., Rahway, N.J.

[21] Appl. No.: 493,595

[22] Filed: Mar. 15, 1990

[51] Int. Cl.[5] .................... C07F 7/18; C07D 309/10
[52] U.S. Cl. .................................. 549/214; 549/292; 544/69; 544/149; 544/584; 544/226; 544/374; 546/14; 546/206
[58] Field of Search .............. 549/214, 292; 514/460; 544/229, 234, 69, 149, 58.4; 548/517, 406; 546/14, 206

[56] References Cited

U.S. PATENT DOCUMENTS 4,876,279 10/1989 Lee et al. ............................ 549/292
4,921,974 5/1990 Duggan ............................... 549/292
4,963,538 10/1990 Duggan et al. ..................... 549/292

OTHER PUBLICATIONS

Kuo et al., *J. Org. Chem.*, "Reductive Transformation of Cyclopropanation of Mevinolin (6α-Methylcompactin)", 48, 1991-1998 (1983).
Greene, "*Protective Groups in Organic Synthesis,*" pp. 39-50 (1981), John Wiley & Sons, New York.
Applequist, *J. Am. Chem. Soc.*, 94, 4272 (1972).
Buchi et al., *J. Am. Chem. Soc.*, 91, 6473 (1969).
Evans et al, *J. Org. Chem.*, 54, 2440 (1989).
Matteson et al, *Tetrahedron Lett.*, 449 (1980).
M. Schroder, *Chem. Rev.*, 80, 187 (1980).
Matteson et al, *J. Org. Chem.*, 54, 2742 (1989).

*Primary Examiner*—Richard L. Raymond
*Assistant Examiner*—Mark W. Russell
*Attorney, Agent, or Firm*—Melvin Winokur; Joseph F. DiPrima

[57] ABSTRACT

This invention discloses novel intermediates and novel process for their preparation where said intermediates are useful for the preparation of 5-oxygenated derivatives (T) of lovastatin and analogs thereof at the 8-acyl side chain and 6-position of the polyhydronaphthyl ring. Said derivatives of lovastatin (T) and analogs thereof are useful in treating hypercholesterolemia and are disclosed in the U.S. Pat. No. 4,963,538.

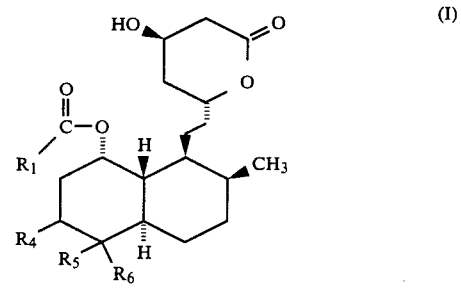

4 Claims, No Drawings

PROCESSES AND INTERMEDIATES FOR THE PREPARATION OF 5-OXYGENATED HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR (lovastatin), now commercially available, is one of a group of very active antihypercholesterolemic agents that function by limiting cholesterol biosynthesis by inhibiting the enzyme, HMG CoA reductase. In addition to the natural fermentation products, mevastatin and lovastatin, there are a variety of semi synthetic and totally synthetic analogs thereof.

The naturally occurring compounds and their semi-synthetic analogs have the following general structural formulae:

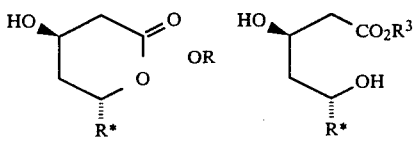

wherein:

$R^3$ is hydrogen, $C_{1-5}$ or $C_{1-5}$ alkyl substituted with a member of the group consisting of phenyl, dimethylamino, or acetylamino; and $R^*$ is

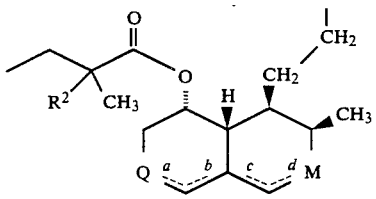

wherein Q is $$R^5-\underset{\underset{CH_3}{|}}{\overset{|}{C}}-$$

or $R^5$—CH; $R^5$ is H or OH; M is —$CHR^6$, $R^6$ is hydrogen or hydroxy;

$R^2$ is hydrogen or methyl; and a, b, c, and d represent single bonds, one of a, b, c or d represents a double bond, or both a and c or both b and d represent double bonds provided that when a is a double bond, Q is

or $$-\underset{\underset{H}{|}}{\overset{|}{C}}=$$

and when d is a double bond, M is $$=\underset{\underset{H}{|}}{\overset{|}{C}}.$$

U.K. Patent 2,075,013 discloses semi synthetic hydroxy containing compounds represented by the above general formula wherein $R^*$

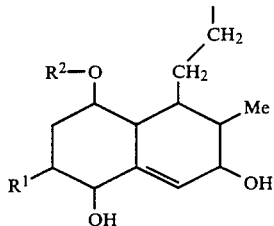

wherein $R^1$ is H or Me, and $R^2$ is H or acyl.

U.S. Patent Application Serial No. 048,136 filed May 15, 1987 discloses 6-substituted compounds of the above general formula wherein $R^*$ is:

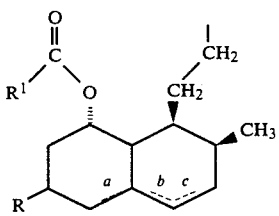

wherein R is $Ch_2OH$, $$\overset{O}{\underset{}{\overset{\|}{CH_2OCR^4}}},$$

$CO_2R^7$ or

and $R^1$, $R^4$, $R^7$, $R^8$ and $R^9$ are broadly defined organic moieties.

U.S. Pat. Nos. 4,604,472 and 4,733,003 disclose compounds of the above formula wherein $R^*$ is:

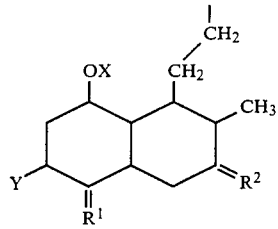

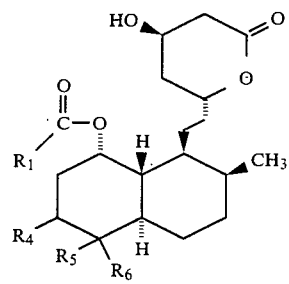

wherein X represents a hydrogen atom or a 2-methylbutyryl group, Y represents a hydrogen atom or a methyl group and $R^1$ and $R^2$ are the same or different and each represents an oxygen atom or a group of formula $=N-OR^3$ where $R^3$ is a hydrogen or alkyl moiety.

Copending U.S. Patent Applications S.N. 213,010 filed June 29 1988, S.N. 322,398 filed Mar. 13, 1989 and now U.S. Pat. No. 4,463,538 and S.N. 250,646 filed Sept. 29, 1988 and now U.S. Pat. No. 4,921,924 disclose compounds of the above general formula wherein $R^*$ is:

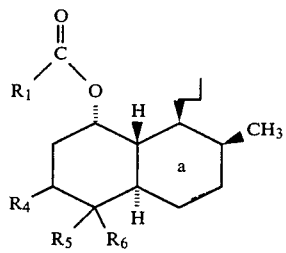

wherein $R^5$ and $R^6$ are H, OH, $OR^7$ or together represent $C=O$. These applications disclose a scheme for preparing a 5-oxo compound which involves treatment of an alkene with NBS to form a bromohydrin and oxidation of the hydroxy moiety of the bromohydrin with pyridinium chlorochromate followed by displacement of the bromine. The disclosed process presents problems of relatively low yield and the employment of environmentally undesirable substances, particularly in the transformation to large scale reactions.

DETAILED DESCRIPTION OF THE INVENTION

This invention relates to novel intermediates and novel processes for their preparation where said intermediates are useful for the preparation of 5-oxygenated derivatives (I) of lovastatin and analogs thereof at the 8-aryl side chain and 6-position of the polyhydronaphthyl ring. Said derivatives of lovastatin (I) and analogs thereof are useful in treating hypercholesterolemia and are disclosed in copending Patent Applications, S.N 213,010 filed June 29, 1988 and S.N. 322,398 filed Mar. 13, 1989 which is now U.S. Pat. No. 4,963,538 Compounds (I) which are HMG-CoA redutase inhibitors may be represented as:

wherein:
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (g) phenyl,
  (h) substituted phenyl in which the substituents are X and Y,
  (i) $C_{1-10}$ alkyl-$S(O)_n$ in which n is 0 to 2,
  (j) $C_{3-8}$ cycloalkyl-$S(O)_n$,
  (k) phenyl-$S(O)_n$,
  (l) substituted phenyl-$S(O)_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substituent is selected from
    (i) halogen
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkyl-$S(O)_n$,
    (ix) $C_{3-8}$ cycloalkyl$S(O)_n$,
    (x) phenyl-$S(O)_n$,
    (xi) substituted phenyl-$S(O)_n$ in which the substituents are X and Y, and
    (xii) oxo,
  (c) $C_{1-10}$ alkyl-$S(O)_n$,
  $C_{3-8}$ cycloalkyl-$S(O)_n$,
  (e) phenyl-$S(O)_n$,
  (f) substituted phenyl-$S(O)_n$ in which the substituents are X and Y,
  (g) halogen,
  (h) hydroxy,
  (i) $C_{1-10}$ alkoxy.
  (j) $C_{1-5}$ alkoxycarbonyl,
  (k) $C_{1-5}$ acyloxy,
  (l) phenyl, and
  (m) substituted phenyl in which the substituents are X and Y;

(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl,
 (C) piperazinyl,
 (d) morphylinyl, and
 (e) thiomorpholinyl; and
(17) $R_5S$ in which $R_5$ is selected from
 (a) $C_{1-10}$ alkyl,
 (b) phenyl, and
 (c) substituted phenyl in which the substituents are X and Y;

$R_4$ is;
(1) hydrogen;
(2) $C_{1-10}$ alkyl; and
(3) substituted $C_{1-10}$ alkyl in which one or more substituents is selected from
 (a) halogen,
 (b) hydroxy,
 (c) $C_{1-10}$ alkoxy
 (d) $C_{1-5}$ alkoxycarbonyl,
 (e) $C_{1-5}$ alkylacyloxy,
 (f) phenylacyloxy,
 (g) phenoxycarbonyl,
 (h) phenyl $C_{1-5}$ alkylacyloxy,
 (i) phenyl $C_{1-5}$ alkoxy,
 (j) amino,
 (k) $C_{1-5}$ alkylamino,
 (l) di($C_{1-5}$ alkyl)amino,
 (m) phenylamino,
 (n) substituted phenylamino in which the substituents are X and Y;
 (o) phenyl $C_{1-5}$ alkylamino.
 (p) substituted phenyl $C_{1-5}$ alkylamino in which the substituents are X and Y,
 (q) $C_{3-8}$ cycloalkyl,
 (r) phenyl,
 (s) substituted phenyl in which the substituents are X and Y,
 (t) phenyl-S(O)$_n$,
 (u) substituted phenyl S(O)$_n$ in which the substituents are X and Y,
 (v) phenyl $C_{1-5}$ alkyl-S(O)$_n$,
 (w) $C_{1-5}$ alkyl-S(O)$_n$;
 (x) phenylaminoacyloxy,
 (y) $C_{1-5}$alkylaminoacyloxy,
 (z) $C_{1-5}$alkylacylamino,
 (aa) di(phenyl$C_{1-5}$alkyl)phosphonyl
 (bb) di($C_{1-5}$alkyl)phosphinyl
(4) $R_4$ together with the carbon atom to which it is attached represents a $C_{3-8}$ carbocyclic ring;

$R_5$ and $R_6$ independently are H, OH, $OR_7$ or $R_5$ and $R_6$ together with the carbon to which they are attached represent C=O or $R_5$ and $R_6$ together with the carbon to which they are attached represent a carbocyclic ring of 4 to 7 atoms; provided that when $R_5$ is H, $R_6$ is OH or $OR_7$, and when $R_5$ is OH, $R_6$ is H, and when $R_5$ is $OR_7$, $R_6$ is H;

$R_7$ is

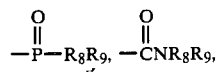

or

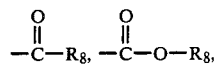

phenyl$C_{1-3}$, alkyl, $C_{1-5}$alkyl;

$R_8$ and $R_9$ independently are H, $C_{1-3}$alkyl, phenyl$C_{1-3}$alkyl or aryl wherein aryl is phenyl naphthyl, pyridyl, furanyl, thienyl or phenyl, naphthyl, pyridyl, furanyl or thienyl substituted with groups X and Y provided that when $R_7$ is

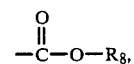

$R_8$ is not H and when $R_7$ is

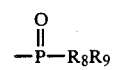

neither $R_8$ nor $R_9$ is H;

X and Y are independently selected from:
 a) OH,
 b) halogen,
 c) trifluoromethyl,
 d) $C_{1-3}$alkoxy,
 e) $C_{1-3}$alkylcarbonyloxy,
 f) phenylcarbonyloxy,
 g) $C_{1-3}$alkoxycarbonyl,
 h) phenyloxy:arbonyl,
 i) hydrogen;
 j) $C_{1-5}$alkyl, The 5-hydroxy derivatives of formula (I) are prepared as shown in scheme 1; additional 5-oxygenated derivatives are prepared from the 5-hydroxy compounds following the descriptions in copending application S.N. 250, 646 filed Sept. 29, 1988.

SCHEME 1

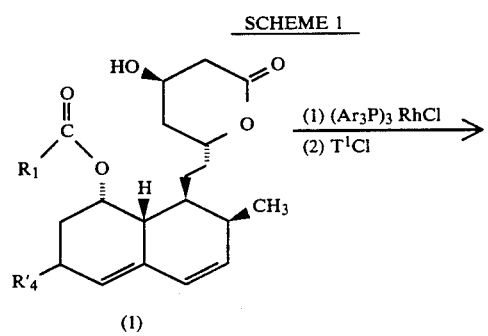

(1)

-continued
SCHEME 1

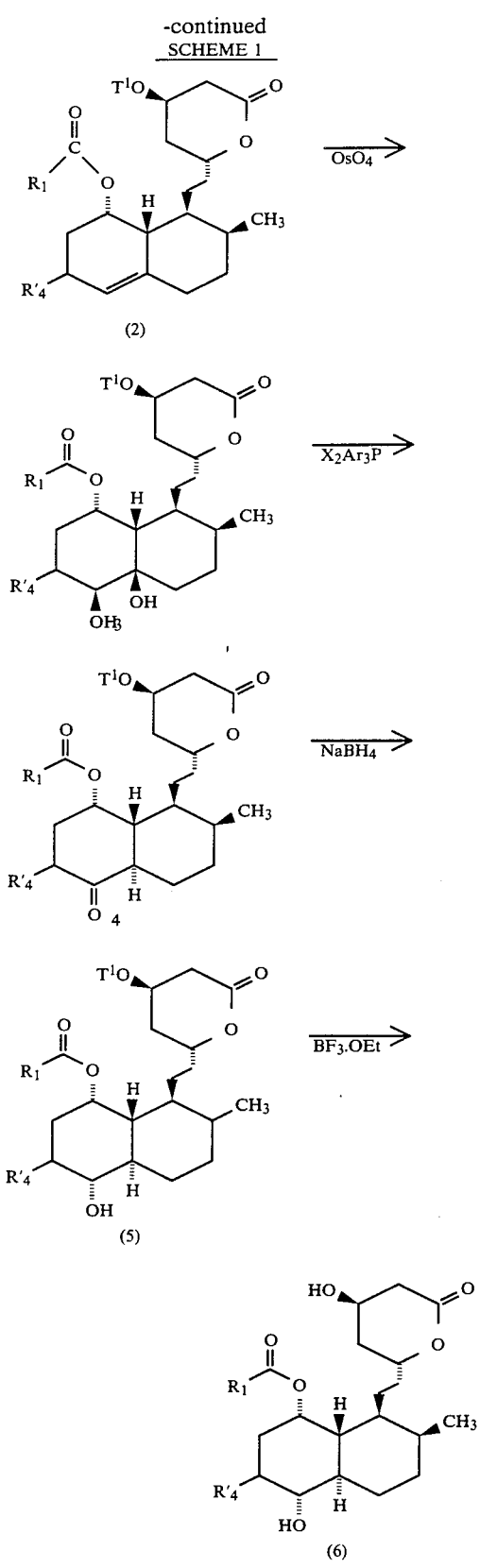

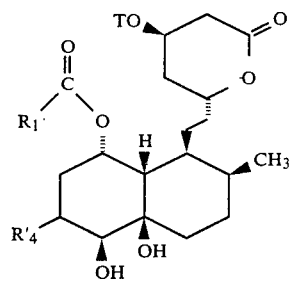

$T^1$ is a hydroxy protecting group.
X is cl or Br.
One embodiment of this invention is the compounds of formula (3):

wherein:
T is H, tert-butyldimethylsily, ter-butyldiphenylsilyl, trimehtylsilyl, triethylsilyl, triiosypropylsilyl, or tetrahydropyranyl;
$R_1$ is selected from:
(1) $C_{1-10}$ alkyl;
(2) substituted $C_{1-10}$ alkyl in which one or more substituent(s) is selected from
  (a) hydrogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkyl-$S(O)_n$ in which n is 0 to 2,
  (j) $C_{3-8}$ cycloalkyl $S(O)_n$,
  (k) phenyl $S(O)_n$,
  (l) substituted phenyl-$S(O)_n$ in which the substituents are X and Y, and
  (m) oxo;
(3) C1-10 alkoxy;
(4) C2-10 alkenyl;
(5) $C_{3-8}$ cycloalkyl;
(6) substituted $C_{3-8}$ :cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkyl-$S(O)_n$,
    (ix) $C_{3-8}$ cycloalkyl-$S(O)_n$,
    (x) phenyl -$S(O)n$,
    (xi) substituted phenyl-$S(O)_n$ in which the substituents are X and Y, and
    (xii) oxy,
  (c) $C_{1-10}$ alkyl-$S(O)_n$,
  (d) $C_{3-8}$ cycloalyl-$S(O)_n$,
  (e) phenyl $S(O)_n$,
  (f) substituted phenyl-$S(O)_n$ in which the substituents are X and Y,
  (g) halogen,
  (h) hydroxy,
  (i) $C_{1-10}$ alkoxy,
  (j) $C_{1-5}$ alkoxycarbonyl, (k) $C_{1-5}$ a:yloxy,
(l) phenyl, and
(m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino; which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R_5S$ in which $R_5$ is selected from
  (a) $C_{1-10}$ alkyl,
  (b) phenyl, and
  (c) substituted phenyl in which the substituents are X and Y;
$R'_4$ is $CH_3$, $CH_2OT$ or H;
X and Y are independently selected from:
a) OH,
b) halogen,
c) trifluoromethyl,
d) $C_{1-3}$alkoxy,
e) $C_{1-3}$alkylcarbonyloxy,
f) phenylcarbonyloxy,
g) $C_{1-3}$alkoxycarbonyl,
h) phenyloxycarbonyl,
i) hydrogen;
j) $C_{1-5}$alkyl.

In one class of this embodiment are compounds (3) wherein:
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalvyl,
  (g) phenyl,
  (h) substituted phenyl in which the substituents are X and Y, and
  (i) oxo;
(3) $C_{3-8}$ cycloalkyl;
(4) substituted $C_{3-8}$ :cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl,
    (vi) phenyl,
    (vii) substituted phenyl in which the substituents are X and Y, and
    (viii) oxo,
  (c) halogen,
  (d) hydroxy,
  (e) $C_{1-10}$ alkoxy,
  (f) $C_{1-5}$ alkoxycarbonyl,
  (g) $C_{1-5}$ a:yloxy,
  (h) phenyl,
  (i) substituted phenyl in which the substituents are X and Y;
(5) phenylamino;
(6) substituted phenylamino in which the substituents are X and Y;
(7) phenyl$C_{1-10}$alyylamino; and
(8) substituted phenyl $C_{1-10}$ alkylamino in which the substituents are X and Y;
X and Y are independently selected from
a) OH,
b) F,
c) trifluoromethyl,
d) $C_{1-3}$alkoxy,
e) hydrogen;
f) $C_{1-5}$alkyl.

In a subclass are the compounds of formula (3) wherein..
$R_1$ is $C_{1-10}$alkyl;
$R'_4$ is $CH_3$ or $CH_2TO$.

Exemplifying this sub:lass are the following compounds (2) selected from the group wherein:
(a) $R_1$ is 2 methyl 2-butyl, $R'_4$ is $CH_3$.
T is tert-butyldimethylsilyl, or H
(b) R is 2 methyl-2-butyl, $R'_4$ is $CH_2OT$, T is tert-butyldimethylsilyl, or H;
(c) $R_1$ is 2-butyl, $R'_4$ is $CH_3$, T is tert-butyldimethylsilyl or H;
(d) $R_1$ is 2-butyl, $R'_4$ is $CH_2OT$, T is tert-butyldimethylsilyl, or H.

A second embodiment of the present invention is the use of compounds(3), to prepare compounds(4): which comprises: treatment of a compound of formula(3):

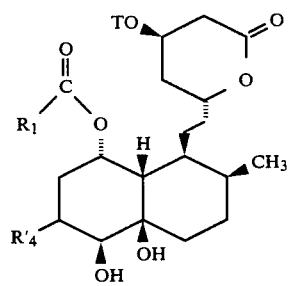

with a dichlorotriphenylphosphorane or metriphenylphosphorane and a weak base, acting as a hydrogen ion scavenger, in a mildly polar aprotic solvent to yield compound (4):

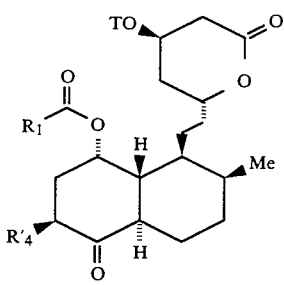

(4)

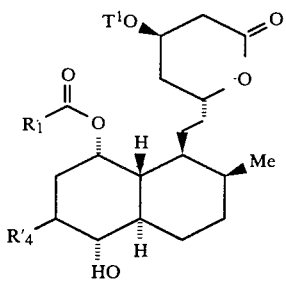

(6)

Illustrating possible weak base are a tertiary amine such as diisopropylethylamine, pyridine, trimethylamine, or triethylamine; or a carbonate or a hydrogen carbonate. The mildly polar aprotic solvent may be any liquid ester such as ethyl acetate or isopropyl acetate or a halogenated hydrocarbon such as dichloromethane or chloroform or a nitrile such as acetonitrile or an ether such as ethyl ether or tetrahydrofuran or a mixture thereof. The preferred base is a tertiary amine. The preferred solvent is acetonitrile or a mixture of acetonitrile with ethyl acetate Intermediates of formula(3) are prepared in a process which comprises:

(i) treating the compound (1) wherein $R_1$, and $R'_4$ are as defined above, with a tris(triarylphosphine)rhodium halide in the presence of hydrogen followed by treatment of the octahydronaphthyl product with a silyl chloride such as t-butyldimethylsilyl chloride or dihydropyran to form a compound of formula (2) wherein $T^1$ represents a silyl protecting group or tetrahydropyran: (aryl herein is phenyl or phenyl substituted with methyl, halogen (Cl or Br) or methoxy).

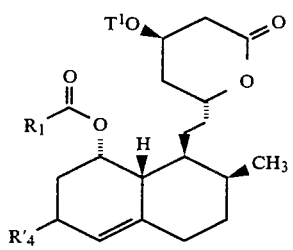

(2)

ii) treating compound (2) with :atalytic osmium tetroxide and a reoxidant such as trimethylamine N-oxide or morpholine-Noxide in an aqueous acetone solvent at reflux temperatures to yield compound (3):

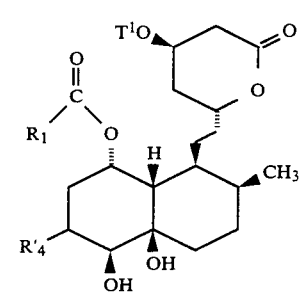

Ketones (4) may be converted to products (X) in a process which comprises treating Ketone (4) with $NaBH_4$ 1 in an ethereal solvent to yield alcohol (6).

followed by removal of the protecting group $T_1$ by treatment with boron trifluoride in acetonitrile to yield product (I).

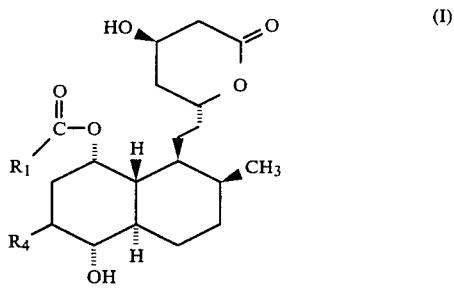

(I)

Compound (2) is prepared from lovastatin by a reduction of the 3,4-double bond following the procedure detailed in copending Patent Application S.N. 092,804, filed Sept. 3, 1987. Where $R_4$ is 6-hydroxymethyl or a protected hydroxymethyl, the conversion of 6-methyl to 6-hydroxymethyl can be accomplished following the procedure in S.N. 048,136, filed May 15, 1987. The hydroxyl group in the lactone ring and at the 6 position of the polyhydronaphthyl ring may be protected (TO) using a silyl prote:ting group su:h as tert-butyldimethylsilyl, following the procedure in U.S. Pat. No. 4,444,784. Where the aryl moiety is other than 2-methylbutyryl the acyl group of lovastatin may be hydrolyzed and the hydroxyl group reesterified with an appropriate alkanoyl halide following the procedure in U.S. Pat. No. 4,444,784. The alkanoyl halide can be formed by standard transformations such as substitution with an alkyl moiety or other appropriate electrophile at an acidic C-H site on an available starting material.

EPO publication 364,206 discloses a method of preparing the 6-α-desmethyl-6-β-methyl lovastatin derivative which can be employed as a starting material in the above scheme. Alternatively, removal of the silyl protecting T of the 6 β-methyl ketone (5) followed by treatment with 1,8-diazabicyclo [5,4,01 undeclene (DBU) results in the 6-β-methyl ketone which after reprotection of the lactone hydroxy group and treatment with $NaBH_4$ gives a mixture of the 6-β-methyl-5(S)-hydroxy compound and the 6-β-methyl-5(R)-hydroxy :compound.

Where the reaction conditions of the above noted chemical transformations would be deleterious to the substituents in the 8-acyloxy moiety, the acetoxy group Can be employed a a protecting group which, after the elaboration of the 5 Position can be removed by hydrolysis to give the 8 hydroxy derivative which then can be acylated according to the general procedures described in U.S. Pat. No. 4,661,483.

Where the product formed by the above described synthetic pathways is not the desired form of that compound, then that product may be subjected to one or more further reactions such as hydrolysis, desilylation, esterification, acylation, ammonolysis or lactonizaton by conventional methods.

The following example illustrates the preparation of intermediate (3), and the compounds of formulae (I) and as such is not to be considered as limiting the invention set forth in the claims appended hereto.

EXAMPLE 1

Preparation of 6(R)-[2 [8(S)-(2,2-dimethylbutyryloxy)-2(S) methyl-5(R)-hydroxy-6(R)-methyl 6,7,8,8a(R)-decahydronaphthyl 1(S)]ethyl]4(R) hydroxy-3,4,5,6-tetrahydro-2H-Dyran-2-one (1)

Step 1

Preparation of 6(R)-[2-(8(S)-(2,2 dimethyl-butryloxy) 2(S) methyl-6(R)-methyl 1,2,3,4, 6,7,8,8a(S) octahydronaphthyl-1(S)]ethyl]-4(R) (R)-hydroxy-3,4,5,6-tetrahydro-2H-pyran-2-one (2)

Isopropanol (10 L) was degassed vacuo at 22° C. followed by pressurizing with nitrogen to 20 psi. This procedure was repeated five times to ensure that oxygen in the solvent was removed. Simvastatin (1 kg, 2.39 moles), Wilkinson's catalyst (tris(triphenyl phosphine) rhodium (I) chloride purified as described below) (100.g, 0.11 mole) and degassed isopropanol (10 L) were charged into a 5-gallon hydrogenator and the mixture was reduced at 250 psi $H_2$ and 40° C. for 72 hours. When the hydrogenation reaction was complete, the reaction mixture was put under 20 psi of nitrogen followed by aging at 0 to 5° C. overnight (10 to 20 hrs) with miminal agitation. The :old mixture was filtered and the filter cake washed with cold isopropanol (500 ml.). Thiourea (10g) was added to the isopropanol filtrate and the mixture aged at 22° C. for 5 hours with agitation. At the end of this aging period, water (20 L) was added followed by cyclohexane (10 L). The two phase system was mixed thoroughly and the layers were separated. The aqueous layer was back-extracted with cyclohexane (500 ml), and the organic layers were combined. To the organic mixture was added methylene chloride (1.5 L) and the mixture was further washed with water (3×10 L). After drying the cyclohexane layer with anhydrous sodium sulfate (200 g), the mixture was filtered and the filter cake further washed with :cyclohexane (200 ml). The volume of the cyclohexane filtrate was reduced in vacuo at ≦40° C. to 5 L. The mixture was warmed rapidly to 70° C and then gradually cooled to 22° C over 4 to 5 hours crystallization occurs during this period. The slurry was further aged at 22° C. for 12 hours. The crystalline product was filtered off and the filter cake washed with cyclohexane (1.5 L) and dried in vacuo at ≦40° C.

Calcd for $C_{25}H_{40}O_5$ C,71.39/ H,9.59/
Found C,71.98 H,9.48,

Purification of Wilkinson's Catalyst

Absolute ethanol (1.2L) was degassed in vacuo at 22° C. followed by pressurizing with nitrogen to 20 psi. The procedure was repeated five times. To the degassed ethanol was added Wilkinson 0.119 mole) and triphenylphosphine (31.2g, 0.119 mole), and the heterogenous mixture was heated at reflux overnight (16 to 24 hours) under a nitrogen atmosphere. The mixture was cooled to 22° C. and filtered under nitrogen. The catalyst filter cake was washed with ethanol (150 ml) and vacuum-dried on the filter.

Step 2:

Preparation of 6(R) [2 (8(S)-(2,2 dimethylbutyroloxy) 2(S)-methyl 6(R) methyl 1,2,3,4, 6,7,8,8a(S) octahydronaphthyl -1(S)]ethyl]4(R)-tert butyldimethylsilyloxy-2H pyran2one. (2)

To solution of the product of Step 1 (100 g, 0.238 mole) and imidazole (25.9 g, 0.380 mole) in acetonitrile (400 ml) at 25° C. was added t-butyl dimethylsilyl chloride (39.4 g 0.262 mole) as a solid. The homogenous mixture was stirred under an atmosphere of nitrogen until the silylation was complete (8 to 10 hours). The reaction mixture was cooled to 0° C. and 1.5 ml of distilled water was added over a period of 5 minutes. The mixture was seeded with 0.1 g of the silylated product followed by the addition of another 1.5 ml of water over 5 minutes. The reaction mixture was maintained at 0° C. and aged for 15 minutes before an additional 397 ml of distilled water was charged dropwise over a period of 1 hour. After the water addition was complete the heterogenous mixture was further aged at 0° for 1 hour and then filtered. The filter cake was washed with 2×100 ml of an ice-cold mixture of $CH_3CN$-$H_2O$ (1:1) followed by 3×100 ml of water. The damp filter cake was dried at room temperature in vacuum with a gentle nitrogen sweep to yield (2) with 92.8% purity as determined by HPLC.

Step 3:

Preparation of 6(R) [2-[8(S) (2,2 dimethyl butyryloxy)-4a(R),5(S)-dihydroxy-2(S),6(R) dimethyl-1,2,3,4,5,6,7,8,8a(R)decahydrona phthyl 1(S)]ethyl]4(R)-tert-butyldimethyl silvloxy 3,4,5,6 tetrahvdyo 2-yan-2-One (3)

A twelve liter, three neck flask, fitted with stirrer, a temperature probe and N2 inlet was charged sequentially with acetone (1.8 L), deionized water (0.6 L), olefin 2, (500.0 g, 0.935 mole) trimethylamine N-oxide (207.8 g, 187 mole), pyridine (75.3 mL, 0.935 mole), and osmium tetroxide solution (prepared by dissolving the solid $OsO_4$ [3.1 g, 0.0122 mole, 1.3 mole %]in 100 mL of acetone). The brown solution was heated at reflux (60°–62° C.) until the reaction was complete (18 h).

The reaction mixture was cooled to room temperature, diluted with ethyl acetate (5.0 L) and cooled in an ice bath to 18° C. Sodium bisulfite solution (1.5 L) was added at such a rate to maintain the temperature <25° C. (exothermic), and the mixture was vigorously stirred for 30 min. The phases were separated, and the aqueous phase was extra:ted with ethyl acetate (5.0 L). The combined organic phases were washed with sodium chloride solution (1.5 L). Florisil (magnesium silicate, 1.0 kg) was added to the organic: phase, and the mixture was agitated for 30 min. The Florisil was removed by filtration, and the cake was washed with ethyl acetate (2.0 L). The filtrate $H_2O$ mg/mL) and concentrated to a final volume of 2.2 L containing the title compound 3.

Step 4:

Preparation of 6(R) [2-[8(S) (2,2- dimethyl-butyroloxy) 2(S)-6(R)-dimethyl-5-oxo 1,2,3, 4a(R),5,6,-7,8,8a(R)-nonahydronaphthyl 1(S)]ethyl]4(R) tert butyldimethylsilyloxy-3,4, 5,6-tetrahydro-2H-pyran-2-one (4)

A dry five liter, three neck flask, fitted with an overhead stirrer, a nitrogen inlet, a temperature probe and a septum was charged with triphenylphosphine (422 g, 1.608 mol) and acetonitrile (1.5 L). To this stirred heterogeneous mixture was added hexachloroethane (381 g, 1.608 mol). in portions over 25 min while maintaining the reaction temperature between 30° and 36° C. When the addition was complete, diisopropylethylamine (560 mL, 416 g, 3.22 mol) was added in one portion.

The phosphorane solution was added to an ethyl acetate (or acetonitrile) solution of diol (416 g in 1.9 L) by cannula with nitrogen pressure, keeping the temperature below 22° C. The vessel containing the phosphorus reagent was rinsed with 100 mL of acetonitrile, and the rinse was transferred by cannula. The blank reaction solution was allowed to come to room temperature and was stirred under nitrogen until the starting material was >99% consumed (24-30 h).

The reaction solution was transferred to a Buchi rotovap, concentrated (with the internal temperature less than 33° C) to one-half volume under vacuum, and the residue converted to an ethyl acetate solution by addition of 6 L of ethyl acetate followed by concentration to a total volume of 2.6–2.8 L. The resulting slurry was transferred to a 12 L, 3-neck flask fitted with an overhead stirrer and a nitrogen inlet. The Buchi flask was rinsed with 500 mL of ethyl acetate, and the rinses transferred, giving a total volume of 3.1 3.3 L. To the resulting vigorously stirred slurry was added 4.5 L of hexanes dropwise over 2 hr at room temperature. When the addition was complete, the mixture was filtered, and &he solids were washed with 4.5 L hexanes.

The cloudy liquors were transferred to a Buchi rotovap with a rinse of 500 mL of hexanes and concentrated under vacuum (internal temperature ≦33° C.) to a volume of 2.8 L. This slurry was transferred with a rinse of 500 mL of hexanes to a 12 L, 3-neck flask fitted with an overhead stirrer and a nitrogen inlet. This rapidly stirred mixture was treated with 4 L hexanes dropwise over 1.2 hr. The resulting mixture was filtered and the solids washed with 1 L of hexanes. HPLC analysis of the filtrate showed that the product ketone 4 was contained in the filtrate.

Step 5:

Preparation of 6(R)-[2-[8(S)-(2,2-dimethyl-butyroloxy) 2(S),6(R)-dimethyl-5(R)-hydroxy 1,2,3,4,4a(R),5,6,7,8,8a(R) decahydronaphthyl 1(S)]ethyyl 4(R) tert butyldimethylsilyloxy3,4,5,6-tertrahydro 2H-vran-2-one. (6).

A five liter, three neck flask, equipped with an overhead stirrer, thermocouple probe, and nitrogen inlet was charged with the ketone as a solution in THF and deionized water (110ml). (The ketone was obtained from the previous reaction as a crude mixture in hexanes. It was concentrated in vacuo, and the solvent turned over to THF by addition of THF followed by distillation of the hexanes then adjusted to a total volume of 2.2 L with THF.) The solution was cooled to −3° C. and sodium borohydride (11.6 g, 0.31 mole) was added as a solid.

When the reaction was complete (1 hr), the reaction flask was fitted with an addition funnel, and a solution of saturated ammonium chloride (1.6 L) was added over 20 minutes. The two phase mixture was stirred for 30 min (internal temperature 5° to 10° C.), and the layers separated.

The tetrahydrofuran/product upper layer was concentrated in vacuo, and dried (KF ≦500 μg/mL) over anhydrous sodium sulfate. The solution Of 240 g of alcohol 6 in 1.4 L of ethyl acetate was concentrated to 1.0 L. The solution was diluted with 3.8 L of hexanes and concentrated (temp <30 C.) to 1.0 L. This procedure was repeated as necessary to obtain an approximate solvent composition in the concentrate of 3:1 hexanes:EtOAc. The concentrate was loaded onto a column of 675 g silica gel (60-250 mesh) packed in 3:1 hexanes:EtOAc. The product was eluted with 3:1 hexanes:EtOAc (approx. 14 L). The appropriate fractions were combined and solvent switched over to hexanes by addition of hexanes followed by distillation The mixture was concentrated to approximately 6.0 L and warmed to 42° C. The solution was allowed to cool to 38° C. and then seeded with product crystals. The mixture was cooled from 38° to 33° C. over a period of 4 hours and then cooled to 22° C. over 6 h, and the resulting slurry filtered. The cake was washed with hexanes (700 ml) and dried in vacuo with a nitrogen sweep to give the title compound 6.

Step 6:

Preparation of 6(R) [2-[8(S)-(2,2 dimethyl butyryloxy)-2(S),6(R)-dimethyl-5(R)-hydroxy 1,2,3,4,4a(R),5,6,7,8,8a(R)-decahydronapthyl 1(S)]ethyl]-4(R)-hydroxy-3,4,5,6, tetrahydro2H vran-2 one. (I)

A dry two liter, three neck flat equipped with an overhead stirrer, a nitrogen inlet, a temperature probe, and a septum was charged with silylated alcohol 6 (50.0 g. 0.0904 mole) and a:etonitrile (500 mL). The clear colorless solution was cooled to 0-3° C. Boron trifluoride etherate (12.5 mL, 0.102 mole,) was added by syringe over 2.0 min, and the resulting pale yellow solution stirred at 0°-3° C. until the reaction was complete (30 min).

The reaction was quenched by the addition of NaHCO$_3$, solution (41.4 mg/mL, aqueous, 3000 mL,) over 5-7 min while keeping the temperature ≦10° C. The mixture was then vigorously stirred for 1.0 h while being allowed to warm to 20° C. The phases were separated, and the pale yellow organic phase washed with NaCl solution (saturated, aqueous, 300 mL). The organic layer was concentrated in vacuo to one half volume (internal temp. ≦30° C.), then switched over to isopropyl acetate by dilution with isopropyl acetate followed by distillation to a final volume of 1250 ml. The solution was washed with deionized water (750 mL) and then transferred to a two liter, three ne:k flask equipped with an overhead stirrer and a distillation apparatus. The residual water was removed by azeotropic vacuum distillation with isopropyl acetate (500 mL, internal temp. ≦30° C.) to a KF ≦500 μg/mL. The volume was adjusted to 280 mL, and the solution was seeded, if necessary. The product was allowed to crystallize at 25° C. for 30 min. Hexanes (840 mL) were then added slowly over 1.0 h. The mixture was aged at 25° C. for 30 min and then at 5° C. overnight (17 h). The product was collected by filtration on a sintered glass funnel, and the crystals washed with cold (−10° C.) isopropyl a:etate in hexanes 25 v/v % (2×30 mL). The white crystalline solids were dried in vacuo at 25° C. with a nitrogen sweep to give the title product. The product purity was assayed by weight pertent against a standard using reverse Phase HPLC: Zorbax C8 analytical column (4.6×250 mm) flow rate =2.0 mL/min, 40:60 acetonitrile/water, U.V. detection at 218 nm, column temperature =45° C. RT =9.7 min.

What is claimed is:

1. A compound of structural formula (3):

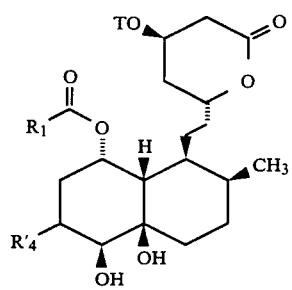

wherein:

T is H, tert-butyldimethylsilyl, tert-butyldiphenylsilyl, trimethylsilyl, triethylsilyl, triiospropylsilyl, or tetrahydropyranyl;

$R_1$ is selected from:
(1) $C_{1-10}$ alkyl;
(2) substituted C1-10 alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl
  (g) phenyl,
  (h) substituted phenyl in which the substituents are X and Y,
  $C_{3-10}$ alkyl-S(O)$_n$ in which n is 0 to 2,
  (j) $C_{3-8}$-cycloalkyl-S(O)$_n$,
  (k) phenylS(O)$_n$,
  substituted phenyl S(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl; one substituted C3-8 cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkyl-S(O)n,
    (ix) C3-8 cycloalkyl-S(O)$_n$,
    (x) phenyl-S(O)$_n$,
    (xi) substituted phenyl-S(O)$_n$ in which the substituents are X and Y, and
    (xii) oxo,
  (c) $C_{1-10}$ alkyl-S(O)$_n$,
  (d) $C_{3-8}$ cycloalkyl-S(O)$_n$,
  (e) phenyl S(O)$_n$,
  (f) substituted phenyl-S(O)$_n$ in which substituents are X and Y,
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R_5S$ in which $R_5$ is selected from
  (a) $C_{1-10}$ alkyl,
  (b) phenyl, and
  (c) substituted phenyl in which the substituents are X and Y;

$R'_4$ is $CH_3$, $CH_2OT$ or H; X and Y are independently selected from:
  a) OH,
  b) halogen,
  c) trifluoromethyl,
  d) $C_{1-3}$alkoxy,
  e) $C_{1-3}$alkylcarbonyloxy,
  f) phenylcarbonyloxy,
  g) $C_{1-3}$alkoxycarbonyl,
  h) phenyloxycarbonyl,
  i) hydrogen;
  j) $C_{1-5}$alkyl.

2. A compound according to claim 1 wherein:

$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y, and (i) oxo;
(3) C3-8 cycloalkyl;
(4) substituted $C_{3-8}$ cycloalkyl in which one substituent is selected from (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl, (vi) phenyl,
(vii) substituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;
X and Y are independently selected from
a) OH,
b) F,
c) trifluoromethyl,
d) $C_{1-3}$alkoxy,
e) hydrogen;
f) $C_{1-5}$alkyl.

3. A compound according to claim 2 wherein:
$R_1$ is $C_{1-10}$ alkyl;
$R'_4$ is $CH_3$ or $Ch_2OT$.

4. A compound according to claim 3 selected from the group wherein:
$R_1$ is 2-methyl-2-butyl, $R'_4$ is $CH_3$, T is tert-butyldimethylsilyl;
(a) $R_1$ is 2-methyl 2-butyl, $R'_4$ is $CH_2OT$ T is tert-butyldimethylsilyl;
(c) $R_1$ is 2-butyl, $R'_4$ is $CH_3$, T is tert-butyldimethylsilyl;
(d) $R_1$ is 2-butyl, $R'_4$ is $CH_2OT$, T is tert-butyldimethylsilyl;
(e) $R_1$ is 2-methyl-2-butyl, $R'_4$ is $CH_3$, T=H;
(f) $R_1$ is 2-methyl-2-butyl, $R'_4$ is $CH_2OT$, T=H;
(g) $R_1$ is 2-butyl, $R'_4$ is $CH_3$, T=H;
(h) $R_1$ is 2-butyl, $R'_4$ is $CH_2OT$, T=H.

* * * * *